United States Patent
Cannas et al.

(10) Patent No.: US 9,403,931 B2
(45) Date of Patent: *Aug. 2, 2016

(54) IRON(III) COMPLEXES AS CATALYSTS FOR POLYURETHANE COMPOSITIONS

(71) Applicant: SIKA TECHNOLOGY AG, Baar (CH)

(72) Inventors: Rita Cannas, Dübendorf (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,964

(22) PCT Filed: Dec. 12, 2012

(86) PCT No.: PCT/EP2012/075218
§ 371 (c)(1),
(2) Date: May 16, 2014

(87) PCT Pub. No.: WO2013/087689
PCT Pub. Date: Jun. 20, 2013

(65) Prior Publication Data
US 2014/0357793 A1    Dec. 4, 2014

(30) Foreign Application Priority Data
Dec. 12, 2011  (EP) .................................... 11193062

(51) Int. Cl.
| | |
|---|---|
| *C08G 18/22* | (2006.01) |
| *C07F 15/02* | (2006.01) |
| *C08G 18/48* | (2006.01) |
| *C07C 235/80* | (2006.01) |
| *C08G 18/76* | (2006.01) |

(52) U.S. Cl.
CPC ............ *C08G 18/222* (2013.01); *C07C 235/80* (2013.01); *C07F 15/02* (2013.01); *C07F 15/025* (2013.01); *C08G 18/22* (2013.01); *C08G 18/48* (2013.01); *C08G 18/4837* (2013.01); *C08G 18/7671* (2013.01)

(58) Field of Classification Search
CPC ............................... C08G 18/22; C08G 18/222
See application file for complete search history.

(56) References Cited

U.S. PATENT DOCUMENTS

| | | | | |
|---|---|---|---|---|
| 4,050,969 A | * | 9/1977 | Oberth | C08G 18/222 149/19.4 |
| 4,871,854 A | * | 10/1989 | Oberth | C06B 45/10 546/7 |
| 6,908,875 B2 | * | 6/2005 | Skinner | C07F 15/025 502/102 |
| 2007/0110644 A1 | | 5/2007 | Kasama et al. | |
| 2009/0092840 A1 | * | 4/2009 | Schlumpf | C08G 18/10 428/423.1 |

FOREIGN PATENT DOCUMENTS

| | | | | |
|---|---|---|---|---|
| GB | WO 2004044027 A1 | * | 5/2004 | .......... B01J 31/0211 |
| WO | WO 2011/117225 A1 | | 9/2011 | |

OTHER PUBLICATIONS

International Preliminary Report on Patentability issued in PCT/EP2012/075218 issued Jun. 17, 2014.
Syamal, "Ferric benzoylacetanilides", *Canadian Journal of Chemistry*, vol. 47, 1969, pp. 1693-1696.
International Search Report issued in International Application No. PCT/EP2012/075218 mailed Apr. 2, 2013.
Oct. 8, 2015 Office Action issued in Chinese Application No. 201280060954.0.

* cited by examiner

*Primary Examiner* — Michael L Leonard
(74) *Attorney, Agent, or Firm* — Oliff PLC

(57) ABSTRACT

The present invention relates to iron (III) complexes of the formula Fe(L)x(Y)3-x, where the ligand L has the formula (I). Such complexes are especially suitable as a catalyst for two-component polyurethane compositions. The invention also relates to two-component polyurethane compositions comprising at least one polyisocyanate as the first component, at least one polyol as the second component and at least one iron (III) complex of this kind as a catalyst. In addition, the invention relates to various uses of these two-component polyurethane compositions.

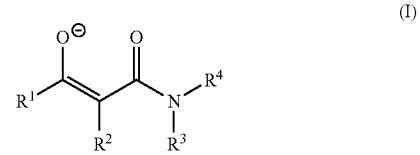

(I)

11 Claims, No Drawings

IRON(III) COMPLEXES AS CATALYSTS FOR POLYURETHANE COMPOSITIONS

TECHNICAL FIELD

The present invention relates to the field of polyurethane compositions and catalysts for polyurethane compositions.

PRIOR ART

Polyurethane compositions are well known, and are used in a multitude of fields. Traditionally, the industrial world distinguishes between one-component and two-component polyurethane compositions. One-component polyurethane compositions cure under the influence of air humidity. Two-component polyurethane compositions contain a curing component as the second component, which contains essentially polyamines and/or polyols. In both cases, compounds or prepolymers that contain isocyanate groups are used.

Catalysts are added to accelerate curing. Although a multitude of polyurethane catalysts are known, a majority of these are not particularly selective with respect to the urethanization reaction, i.e., the reaction of alcoholic OH groups with isocyanate groups, and catalyze instead, to a greater or lesser extent, other reactions of the isocyanate group, such as allophanate and biuret formation or cyclotrimerization. More particularly, in most cases the urethanization reaction is in competition with the reaction of the isocyanate groups with water, which liberates gaseous carbon dioxide, forming urea groups. With many polyurethane compositions, particularly when used as adhesives and sealants, as coatings or as casting resin, this secondary reaction is troublesome, since it leads to the formation of bubbles during curing and therefore to poor dimensional stability, poorer adhesion, lower mechanical strength, unsatisfactory aesthetics and poorly reproducible results. The water which is responsible for bubble formation comes either from the residual water content of the constituents of the composition, in particular, the polyols and the filler materials, which are more or less moist, even after drying processes, and which have a typical residual water content of 0.01 to 0.5 wt/%, or from ambient humidity, which penetrates by diffusion from the air or from the substrates into the composition, which occurs particularly in the presence of high air humidity, porous substrates and/or hydrophilic polyols, such as the polyether polyols that are frequently used in practical applications. Amine catalysts, for example tertiary amines, and tin catalysts, for example dialkyl tin carboxylates, which are widely used in practical applications, frequently result in pronounced bubble formation. Moreover, as a result of the residual water content of the polyurethane composition, catalysts that are susceptible to hydrolysis, such as bismuth carboxylates, for example, become deactivated when the composition is retained for extended periods of time prior to use (storage), which has a negative impact on the rate of curing and on mechanical properties. With some known catalysts, for example dialkyl tin carboxylates, the stability of the cured composition under thermal stress is unsatisfactory, with the catalyst causing molecular weight degradation, i.e., a depolymerization, with a loss of mechanical strength. Furthermore, many of the known catalysts are solid at room temperature, and are poorly soluble in the polyurethane starting materials or softening agents, so that in order to use these catalysts in compositions that cure at room temperature, organic solvents must be used. Finally, some of the known catalysts, particularly those based on heavy metal compounds, cause concern in terms of toxicology.

The use of iron(III) complexes as catalysts for curable substances, for example, polyurethane compositions, is known. For instance, U.S. Pat. No. 4,871,854 and US 2007/00110644 describe iron(III) tris(acetylacetonate) as a catalyst. However, this substance is crystalline, has a high melting point, and is soluble in the composition only in small quantities, so that organic solvents must be used or processing must be conducted at high curing temperatures in order to take advantage of the catalytic potential. Although the iron (III) carboxylates, such as iron(III)-tris(2-ethylhexanoate), which are also known as catalysts, are more readily soluble, they are also susceptible to hydrolysis and are therefore relatively quickly deactivated during storage.

DESCRIPTION OF THE INVENTION

The object of the present invention is to overcome the above-described disadvantages of the prior art. More particularly, the object of the present invention is to provide a catalyst that leads to an improvement in the resulting properties and/or to a balance ratio thereof.

The catalyst is to be characterized by high catalytic activity and selectivity with respect to the urethanization reaction, i.e., the reaction of alcoholic OH groups with isocyanate groups, thus enabling a rapid synthesis of a mechanically high-quality polyurethane polymer from polyfunctional alcohols (polyols) and polyisocyanates, the negative impact on which by humidity is minimized. The catalyst is also to possess adequate resistance to hydrolysis, so that it can be held under customary storage conditions, i.e., at room temperature or at slightly elevated temperatures, for several months in a polyol composition that contains residual water, without significant loss of activity. Furthermore, the catalyst is to lower the thermal stability of the cured polyurethane polymer as little as possible. Beyond this, the catalyst is to be fluid at room temperature or at slightly elevated temperatures and/or is to be readily soluble in the polyurethane starting materials or in softening agents, so that it can easily be used in solventless systems that cure at room temperature. Finally, the catalyst is to have the lowest possible toxicity.

Unexpectedly, a novel iron(III) complex according to claim 1 and having the desired properties has now been found. The novel iron(III) complex has the formula $Fe(L)_x(Y)_{3-x}$, in which x stands for 1, 2 or 3, Y stands for a uninegatively charged ligand, and L stands for a ligand of formula (I),

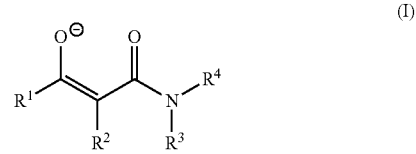

(I)

in which $R^1$ and $R^2$ independently stand for a hydrogen group or for a monovalent saturated or unsaturated hydrocarbon group containing 1 to 10 carbon atoms, or together stand for a divalent alkylene group having 3 to 6 carbon atoms, and $R^3$ and $R^4$ independently stand for a hydrogen group or for a monovalent saturated hydrocarbon group, optionally containing heteroatoms and having 1 to 12 carbon atoms, or together stand for a divalent alkylene group, optionally containing heteroatoms and having 3 to 6 carbon atoms.

The ligand L of formula (I) formally has a uninegative charge that is delocalized over the 1,3-ketoamide structure. It can therefore be depicted in various limit structures, for example, in the limit structures shown below. All possible limit structures of the ligand L of formula (I) are considered to be equivalent in the scope of the present invention.

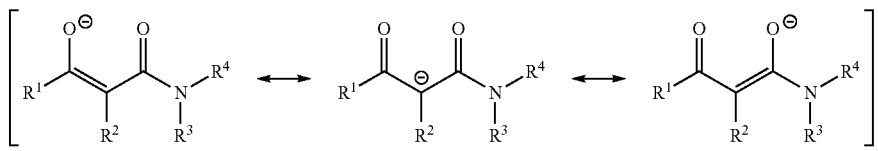

The ligand Y is any uninegatively charged ligand, in particular, a suitable organic anion, preferably a carbonylate, particularly preferably a 1,3-dicarbonylate, for example, acetylacetonate or 2,2,6,6-tetramethylheptane-3,5-dionate.

The iron(III) complex of the formula $Fe(L)_x(Y)_{3-x}$ according to the invention with iron as its central atom and ligands L and optionally Y coordinately bonded to the iron is neutral and contains at least one ligand L of formula (I).

If the iron(III) complex according to the invention has two or three ligands L, i.e., x=2 or 3 in the above formula, the ligands L can be the same or different.

In the iron(III) complex according to the invention, in the formula $Fe(L)_x(Y)_{3-x}$ x preferably stands for 3, as these complexes are particularly stable. The three ligands L of formula (I) can be the same or different. Three of the same ligands L of formula (I) are particularly preferred.

In formula (I), $R^1$ and $R^2$ independently stand for a hydrogen group or for a monovalent saturated or unsaturated hydrocarbon group containing 1 to 10 carbon atoms, or together stand for a divalent alkylene group having 3 to 6 carbon atoms.

The monovalent saturated hydrocarbon group having 1 to 10 carbon atoms is preferably an alkyl group having 1 to 4 carbon atoms, more particularly, a methyl group or a butyl group. These have the advantage that the complex tends to be fluid or readily soluble. The monovalent unsaturated hydrocarbon group preferably is also an aryl group, more particularly, a phenyl group.

Particularly preferably, $R^2$ is a hydrogen group, since the complex tends to be particularly stable as a result.

A divalent alkylene group having 3 to 6 carbon atoms is understood as a group of the formula —$(CH_2)_n$—, in which n stands for 3 to 6.

$R^1$ and $R^2$ together preferably form a divalent alkylene group having 3 to 4 carbon atoms, particularly having 3 carbon atoms.

$R^3$ and $R^4$ independently stand for a hydrogen group or for a monovalent saturated hydrocarbon group, optionally containing heteroatoms and having 1 to 12 carbon atoms, or together stand for a divalent alkylene group, optionally containing heteroatoms and having 3 to 6 carbon atoms.

The monovalent saturated hydrocarbon group having 1 to 12 carbon atoms is preferably an alkyl group having 1 to 8 carbon atoms, particularly preferably a methyl group, an ethyl group, a propyl group, an isopropyl group, a butyl group, an isobutyl group, a hexyl group, a 2-methyl-pentyl group, an octyl group, or a 2-ethyl-hexyl group. This has the advantage that the complex tends to be fluid or readily soluble. Preferably, the monovalent saturated hydrocarbon group having 1 to 12 carbons atoms can also be a cycloalkyl group having 5 to 6 carbon atoms, particularly preferably having 6 carbon atoms. The monovalent saturated hydrocarbon group with heteroatoms is preferably a hydroxyalkyl group containing 1 to 4 carbon atoms, particularly preferably a 2-hydroxyethyl group or 2-hydroxypropyl group. This has the advantage that the complex tends to be fluid or readily soluble as a result, and the ligand can be covalently bonded into the polymer during curing. Also preferred is an alkylether group having 1 to 4 carbon atoms, particularly preferably a 2-methoxyethyl group or a 2-(2-methoxy)ethoxyethyl group, since the complex tends to be fluid or readily soluble as a result.

$R^3$ together with $R^4$ can preferably also form a divalent alkylene group of the formula —$(CH_2)_n$—X—$(CH_2)_n$—, in which X=O, NR, in which R is a monovalent alkyl group having 1 to 4 carbon atoms, or S and n=2 to 4. Particularly preferably, n=2 and X=O or NR.

The selection of the preferred groups in the ligands L of formula (I) is preferably based upon the fact that the corresponding 1,3-ketoamides, which are used as starting materials for producing the iron(III) complex of the formula $Fe(L)_x(Y)_{3-x}$ according to the invention, can be easily produced and/or are commercially available and are therefore cost-effective.

Preferred are iron(III) complexes of the formula $Fe(L)_3$ having three of the same ligands L of formula (I), in which $R^1$ to $R^4$ have the meanings indicated in the table.

| | $R^1$ | $R^2$ | $R^3$ | $R^4$ |
|---|---|---|---|---|
| (1) | Alkyl group having 1-4 carbon atoms | Hydrogen group | Alkyl group having 1-8 carbon atoms | Alkyl group having 1-8 carbon atoms |
| (2) | Phenyl group | Hydrogen group | Alkyl group having 1-8 carbon atoms | Alkyl group having 1-8 carbon atoms |
| (3) | Alkyl group having 1-4 carbon atoms | Hydrogen group | Alkylether group having 1-4 carbon atoms | Alkylether group having 1-4 carbon atoms |
| (4) | Alkylene group having 3-6 carbon atoms | | Alkyl group having 1-8 carbon atoms | |
| (5) | Alkyl group having 1-4 carbon atoms | Hydrogen group | Alkylene group of the formula —$(CH_2)_n$—X—$(CH_2)_n$— with X = O or NR and n = 2 | |
| (6) | Alkyl group having 1-4 carbon atoms | Hydrogen group | Cycloalkyl group having 5-6 carbon atoms | Alkyl group having 1-8 carbon atoms |
| (7) | Alkyl group having 1-4 carbon atoms | Hydrogen group | Alkyl group having 1-8 carbon atoms | Cycloalkyl group having 5-6 carbon atoms |
| (8) | Phenyl group | Hydrogen group | Alkylene group of the formula (—$CH_2)_n$—X—$(CH_2)_n$— with X = O or NR and n = 2 | |

Particularly preferred in this case are the Fe(III) complexes (1), (2) and (3), most particularly preferably the Fe(III) complex (1).

Most particularly preferred are iron(III) complexes of the formula $Fe(L)_3$ having three of the same ligands L of formula (I), in which $R^1$ stands for a methyl group, $R^2$ stands for a hydrogen group and $R^3$ and $R^4$ each stand for an ethyl group, or $R^1$ stands for a methyl group, $R^2$ stands for a hydrogen group and $R^3$ and $R^4$ each stand for an alkylether group having 3 carbon atoms, or $R^1$ stands for a phenyl group, $R^2$ stands for a hydrogen group and $R^3$ and $R^4$ stand for a butyl group, or $R^1$ stands for a butyl group, $R^2$ stands for a hydrogen group and $R^3$ and $R^4$ each stand for a butyl group. The iron(III) complex of the formula $Fe(L)_3(Y)_{3-x}$ according to the invention is produced by reacting a 1,3-ketoamide of the formula

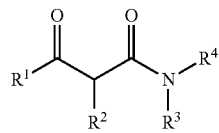

with $R^1$, $R^2$, $R^3$ and $R^4$, as defined above, with an iron(III) salt or iron(III) complex. Preferred is the use of iron(III)-tris (acetylacetonate) and iron(III)-tris-(2-ethylhexanoate).

The 1,3-ketoamide can be used stoichiometrically or hyperstoichiometrically. With a hyperstoichiometric use of the 1,3-ketoamide, the iron(III) complex according to the invention tends to have increased stability in hydrolysis and a lower viscosity. The stoichiometric ratio of the iron(III) salt or the iron(III) complex to the 1,3-ketoamide preferably ranges from 1:3 to 1:6.

The preferably dried iron(III) salt or the iron(III) complex is mixed with the 1,3-ketoamide and the mixture is preferably heated to a temperature of 50 to 130° C., in particularly approximately 90° C., while being stirred over a period of 1 to 24 hours, preferably approximately 4 hours. The reaction mixture is then preferably freed of volatile constituents in a vacuum.

The iron(III) salt or the iron(III) complex can also be mixed in the form of a solution, preferably in ethylhexanoic acid, with a 1,3-ketoamide, and heated to 50 to 130° C., preferably approximately 80° C., preferably while being stirred, for a period of 1 to 24 hours, preferably approximately 3 hours. The reaction mixture is then preferably cooled to room temperature.

The iron(III) complexes according to the invention can be used as catalysts for curable substances, preferably for polyurethane compositions. The iron(III) complex according to the invention accelerates the curing of curable substances, which have reactive groups that are capable of cross-linking reactions. The iron(III) complex according to the invention preferably accelerates the curing of two-component polyurethane compositions, which cross-link with themselves and optionally under the influence of humidity over blocked or particularly free isocyanate groups. In this case, especially the urethanization reaction, i.e., the reaction of isocyanate groups with alcoholic OH groups, is accelerated. The compositions to be cross-linked can also contain additional reactive groups that are capable of cross-linking reactions, such as alkoxysilane groups in particular. These are preferably trialkoxysilane groups, such as those that are contained, for example, in silane adhesives.

The iron(III) complexes according to the invention can advantageously be used as catalysts in two-component polyurethane compositions. Such compositions comprise, in addition to the iron(III) complex according to the invention, a polyol as the first component and a polyisocyanate as the second component.

A composition is referred to as "two-component" if the constituents thereof are present in the form of two different components, which are stored in separate containers, and each of which is stable in storage. Shortly before or during the application of the composition, the two components are mixed with one another, whereupon the mixed composition cures, with curing occurring or being completed under certain circumstances under the influence of humidity and/or elevated temperature.

Substance names that begin with "poly", such as polyol or polyisocyanate, refer to substances that formally contain two or more of the functional groups present in the name thereof per molecule.

The term "polyisocyanate" comprises compounds having two or more isocyanate groups, regardless of whether these are monomeric diisocyanates, oligomeric polyisocyanates or isocyanate groups having polymers.

Suitable polyisocyanates include, for example, polyisocyanates in the form of a monomeric diisocyanate or triisocyanate or an oligomer of a monomeric diisocyanate or a derivative of a monomeric diisocyanate.

Suitable monomeric diisocyanates or triisocyanates include, for example, 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine diisocyanate and lysinester diisocyanate, cyclohexan-1,3 diisocyanate and -1,4-diisocyanate, 1-methyl-2,4- and -2,6-diisocyanato-cyclohexane and any mixtures of these isomers, 1-isocyanato-3,3,5-trimethyl-5-isocyanatomethyl-cyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis-(isocyanatomethyl)-cyclohexane, m- and p-xylylene diisocyanate (m- and p-XDI), m- and p-tetramethyl-1,3- and -1,4-xylylene diisocyanate (m- and p-TMXDI), bis-(1-isocyanato-1-methylethyl)-naphthalene, dimeric and trimeric fatty acid isocyanates, such as 3,6-bis-(9-isocyanatononyl)-4,5-di-(1-heptenyl)-cyclohexene (dimeryl diisocyanate), α,α,α',α',α'',α''-hexamethyl-1,3,5-mesitylene triisocyanate, 2,4- and 2,6-toluylene diisocyanate and any mixtures of these isomers (TDI), 4,4'-, 2,4'- and 2,2'-diphenylmethane diisocyanate and any mixtures of these isomers (MDI), mixtures of MDI and MDI homologues (polymeric MDI or PMDI), 1,3- and 1,4-phenylene diisocyanate, 2,3,5,6-tetramethyl-1,4-diisocyanatobenzol, 1,5-naphthalene diisocyanate (NDI), 3,3'-dimethyl-4,4'-diisocyanatodiphenyl (TODI), dianisidine diisocyanate (DADI), 1,3,5-tris-(isocyanatomethyl)-benzene, tris-(4-isocyanatophenyl)-methane and tris-(4-isocyanatophenyl)-thiophosphate.

Preferred polyisocyanates are commercially available diisocyanates. Particularly preferable are HDI, IPDI, TDI and MDI and oligomers of diisocyanates and polyurethane polymers having isocyanate groups (NCO prepolymers).

The following commercially available polyols or mixtures thereof can be used as polyols, for example:

Polyoxyalkylene polyols, also called polyether polyols or oligoetherols, which are polymerization products of ethylene oxide, 1,2-propylene oxide, 1,2- or 2,3-butylene oxide, oxetane, tetrahydrofuran or mixtures thereof, optionally polymerized with the help of a starter molecule having two or more active hydrogen atoms such as water, ammonia or compounds having multiple OH or NH groups, such as 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerin, aniline, and mixtures of the aforementioned compounds. Both polyoxyalkylene polyols that have a low degree of unsaturation (measured according to ASTM D-2849-69 and indicated as milliequivalents of unsaturation per gram of polyol (mEq/g)), produced, for example, with the help of so-called double metal cyanide complex catalysts (DMC catalysts), and polyoxyalkylene polyols that have a higher degree of unsaturation, produced, for example, using anionic catalysts such as NaOH, KOH, CsOH or alkali alcoholates can be used.

Particularly suitable are polyoxyalkylene diols or polyoxyalkylene triols, in particular, polyoxyethylene and polyoxypropylene diols and triols. Particularly suitable are polyoxyalkylene diols and triols having a degree of unsaturation of less than 0.02 meq/g and having a molecular weight ranging from 1,000-30,000 g/mol, and polyoxypropylene diols and triols having a molecular weight of 400-8,000 g/mol.

Also particularly suitable are so-called ethylene oxide terminated ("EO-endcapped", ethylene oxide-endcapped) polyoxypropylene polyols. The latter are special polyoxypropylene polyoxyethylene polyols, which are obtained, for example, by further alkoxylating pure polyoxypropylene polyols, more particularly, polyoxypropylene diols and triols, upon completion of the polypropoxylation reaction with ethylene oxide, and which therefore contain primary hydroxyl groups.

Styrene acrylonitrile-grafted or acrylonitrile-methylmethacrylate-grafted polyether polyols.

Polyester polyols, also called oligoesterols, produced according to known methods, in particular, the polycondensation of hydroxycarboxylic acids or the polycondensation of aliphatic and/or aromatic polycarboxylic acids with divalent or polyvalent alcohols.

Particularly suitable polyester polyols include those which are produced from divalent to trivalent, particularly divalent alcohols, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexane dimethanol, dimeric fatty acid diol (dimerdiol), hydroxypivalinic acid neopentyl glycol ester, glycerin, 1,1,1-trimethylol propane or mixtures of the aforementioned alcohols, with organic dicarboxylic or tricarboxylic acids, in particular, dicarboxylic acids, or the anhydrides or esters thereof, for example, succinic acid, glutaric acid, adipic acid, trimethyladipic acid, suberic acid, azelaic acid, sebacic acid, dodecanoic dicarboxylic acid, maleic acid, fumaric acid, dimeric fatty acid, phthalic acid, phthalic acid anhydride, isophthalic acid, terephthalic acid, dimethyl terephthalate, hexahydrophthalic acid, trimellitic acid and trimellitic acid anhydride, or mixtures of the aforementioned acids, and polyester polyols of lactones, for example, of ε-caprolactone, and starters such as the aforementioned divalent or trivalent alcohols.

Polycarbonate polyols, such as those that can be produced, for example, by reacting the aforementioned alcohols—used for synthesizing the polyester polyols—with dialkyl carbonates, diaryl carbonates or phosgene.

At least two block copolymers that carry hydroxyl groups and have at least two different blocks having a polyether-, polyester- and/or polycarbonate structure of the type described above, particularly polyether polyester polyols.

Polyacrylate polyols and polymethacrylate polyols.

Polyhydroxyfunctional fats and oils, for example, natural fats and oils, in particular, castor oil; or polyols obtained by chemically modifying natural fats and oils—so-called oleochemical polyols—, for example, the epoxy polyesters and/or epoxy polyethers obtained by epoxidization of unsaturated oils and subsequent ring scission with carboxylic acids and/or alcohols, or polyols obtained by hydroformylation and hydrogenation of unsaturated oils; or polyols obtained from natural fats and oils by means of degradation processes such as alcoholysis or ozonolysis and subsequent chemical bonding, for example, by transesterification or dimerization, of the degradation products or derivatives thereof obtained thereby. Suitable degradation products of natural fats and oils include particularly fatty acids and fatty alcohols, and fatty acid esters, particularly the methyl esters (FAME), which can be derived, for example, by hydroformylation and hydrogenation to hydroxy fatty acid esters.

Polyhydrocarbon polyols, also called oligohydrocarbonols, such as polyhydroxy functional polyolefins, polyisobutylenes, polyisoprenes; polyhydroxy functional ethylene-propylene copolymers, ethylene-butylene copolymers or ethylene-propylene-diene copolymers; polyhydroxy functional polymers of dienes, in particular, of 1,3-butadiene, which can also be produced particularly by means of anionic polymerization; polyhydroxy functional copolymers of dienes such as 1,3-butadiene or diene mixtures and vinyl monomers such as styrene, acrylonitrile, vinyl chloride, vinyl acetate, vinyl alcohol, isobutylene and isoprene, for example, polyhydroxy functional acrylonitrile/butadiene copolymers, such as those that can be produced, for example, from epoxides or amino alcohols and carboxyl-terminated acrylonitrile/butadiene copolymers; and hydrogenated polyhydroxy functional polymers or copolymers of dienes.

The above-stated polyols preferably have an average molecular weight of 250-30,000 g/mol, in particular, of 400-20,000 g/mol, and further preferably have an average OH functionality ranging from 1.6 to 3.

"Molecular weight" in the case of oligomers or polymers is always understood as the molecular weight average $M_n$.

Particularly preferred is the use of polyether polyols, preferably polypropylene polyols and polyethylene-polypropylene mixed polyols, and polyester polyols and polycarbonate polyols.

The iron(III) complex according to the invention is preferably present in the first component, which has the advantage that the polyisocyanate in the second component, which polyisocyanate is sensitive to catalytically active compounds, is not adversely affected in terms of its stability in storage (shelf-life).

The iron(III) complex according to the invention can be used either as a sole catalyst or together with other catalysts, for example, bismuth, tin or zirconium compounds or tertiary amines.

The two-component polyurethane composition according to the invention can optionally contain additional routinely used auxiliary and supplementary agents, for example, pigments, softening agents and/or diluents, curing agents, crosslinking agents, chain extenders, additional catalysts, adhesive agents, stabilizers, rheological additives and drying agents, etc.

The iron(III) complex according to the invention, viewed as a quantity of elemental iron, is preferably present in the two-component polyurethane composition according to the invention in a quantity of 0.001 to 1 wt/%, particularly preferably in a quantity of 0.005 to 0.5 wt/%, and most particularly preferably in a quantity of 0.01 to 0.2 wt/%, referred to the weight of the composition. Excessive quantities will result in an overly short open time and/or processing time for the composition, whereas the use of insufficient quantities will result in the disadvantage that the composition is too weakly catalyzed and therefore cures too slowly, incompletely and/or with defects. In the two-component polyurethane composition according to the invention, the iron(III) complex according to the invention makes up 0.01 to 10, preferably 0.05 to 5, and particularly preferably 0.1 to 2 mmol equivalent iron atoms to 100 g of the composition.

As was already mentioned above, the iron(III) complex according to the invention is relatively active and also relatively selective with respect to the urethanization reaction. The iron(III) complex according to the invention is thus distinguished from known iron(III) complexes by a substantially higher catalytic activity. The two-component polyurethane composition according to the invention generally cures rapidly, particularly in significantly shorter curing times than when known iron(III) complexes are used. However, the selectivity of the iron(III) complex according to the invention does not suffer from increased activity; curing occurs without the formation of bubbles, even under unfavorable conditions such as high temperature, high ambient humidity and/or high residual water content of the composition, and when polyols having secondary OH groups or hydrophilic polyols are used. The iron(III) complex according to the invention is relatively thermally and hydrolytically stable, breaks down only slowly in a polyol containing residual water, and therefore maintains its catalytic activity even during extended periods of storage. Nevertheless, the use of the iron(III) complex according to the invention results in good stability of the cured polyurethane composition under thermal stress. Moreover, the iron(III) complex according to the invention is fluid at room temperature and/or is readily soluble in softening agents or polyols, and can therefore be readily used in systems that cure at room temperature, particularly without the use of volatile organic solvents (VOC). Finally, the iron(III) complex according to the invention has relatively low toxicity.

The two-component polyurethane composition according to the invention can be used in a multitude of areas, for example, as casting compound, sealant, adhesive, covering, coating, varnish, undercoating, hard foam, soft foam, molded articles, elastomer, fiber, film or membrane for constructional and industrial applications, for example, as electrical casting compound, putty compound, seam sealant, cavity sealant, joint sealant, mounting adhesive, panel adhesive, glass adhesive, sandwich element adhesive, laminating adhesive, packaging adhesive, wood adhesive, parquetry adhesive, anchoring adhesive, floor covering and floor coating, balcony and roof coating, concrete protective coating, parking garage coating, pipe coating, anti-corrosion coating, textile coating, wood varnish, decorative varnish, primer, furniture foam, upholstery foam, filter foam, insulating foam, noise damping foam, sealing foam, packaging foam, panel foam, model construction foam, damping elements, sealing elements, tires, wheels, bearings, rollers, conveyor belts, rubber fibers, shoe soles, housings, window molding, implants, foam rubber, etc.

Preferred areas of application are as casting compounds, sealants, adhesives, coverings, coatings, varnishes, undercoatings, molded articles and elastomers for constructional and industrial applications.

In addition to being used in two-component polyurethane compositions, the iron(III) complex according to the invention can also be used as a catalyst or cocatalyst in other curable compounds, for example, in one-component polyurethane compositions, in epoxide resins, acrylates and silicones.

EXAMPLES

Description of Measuring Methods

Infrared spectra were measured using an FT-IR 1600 instrument from Perkin-Elmer (horizontal ATR measuring unit with a ZnSe crystal; measurement window 4000-650 $cm^{-1}$). Liquid samples were applied undiluted as films, solid samples were dissolved in $CH_2Cl_2$. Absorption bands are indicated as wave numbers ($cm^{-1}$).

$^1$H-NMR spectra were measured using a Bruker DPX-300 spectrometer at 300.13 MHz; the chemical shifts δ are indicated in ppm relative to tetramethyl silane (TMS). No differentiation was made between real and pseudo coupling samples.

Viscosity was measured using a thermostatted Physica MCR 300 cone-and-plate viscosimeter (cone diameter 20 mm, cone angle 1°, cone tip-to-plate distance 0.05 mm, shear rate 0.1 to 100 $s^{-1}$).

UV-vis spectra of samples dissolved in dichloromethane (40 mg/l) in 1 cm quartz cuvettes were measured using a Varian Cary 50 type spectrometer, in the wavelength range of 800-200 nm. Extinction maxima $\lambda_{max}$ are indicated in nm and the associated extinction coefficients ε are indicated as $l \cdot g^{-1} \cdot cm^{-1}$, placed between parentheses.

Production of the Iron(III) Complexes

Basic Production Procedure A

Dried iron(III)-tris-(acetylacetonate) and a 1,3-ketoamide (≥3 equivalents/Fe) were mixed in a round-bottomed flask, and the mixture was heated to 90° C. with stirring for a period of 4 hours. The reaction mixture was then freed of the volatile constituents in a vacuum.

Basic Production Procedure B

A solution of iron(III)-(2-ethylhexanoate) in 2-ethylhexanoic acid (6% Fe) was mixed with a 1,3-ketoamide (≥3 equivalents/Fe) in a round-bottomed flask, and was heated to 80° C. with stirring for a period of 3 hours. The reaction mixture was then cooled to room temperature.

Example 1

Iron(III)-tris(N,N-diethyl-3-oxobutanamidate)

3.53 g iron(III)-tris(acetylacetonate) and 4.87 g N,N-diethyl-3-oxobutanamide were reacted according to basic production procedure A. The result was 5.60 g of a red, highly viscous oil.

FT-IR: 2972, 2929, 1638, 1597, 1552, 1497, 1433, 1360, 1308, 1268, 1203, 1163, 1082, 1004, 961, 925, 827, 762, 725, 660.

UV-vis: 442 (0.4). (cf., iron(III)-tris(acetylacetonate): 434 (0.7) and 354 (0.7).)

Example 2

Iron(III)-tris(N,N-diethyl-3-oxobutanamidate)

4.40 g iron(III)-tris(acetylacetonate) and 9.29 g N,N-diethyl-3-oxobutanamide were reacted according to basic production procedure A. The result was 10.70 g of a red oil.

FT-IR: 2970, 2932, 1722, 1637, 1595, 1557, 1512, 1492, 1452, 1432, 1374, 1356, 1309, 1272, 1203, 1163, 1081, 1004, 962, 827, 762, 659.

Example 3

Iron(III)-tris(N,N-diethyl-3-oxobutanamidate)

1.72 g iron(III)-tris(2-ethylhexanoate) and 0.89 g N,N-diethyl-3-oxobutanamide were reacted according to basic production procedure B. The result was 2.61 g of a red oil.
FT-IR: 2955, 2925, 2855, 1725, 1638, 1563, 1515, 1495, 1458, 1377, 1359, 1309, 1275, 1202, 1163, 1097, 1082, 1007, 963, 765, 663.

Example 4

Iron(III)-tris(N,N-bis(2-methoxyethyl)-3-oxobutanamidate)

3.53 g iron(III)-tris(acetylacetonate) and 6.74 g N,N-bis(2-methoxyethyl)-3-oxobutanamide were reacted according to basic production procedure A. The result was 7.69 g of a red, highly viscous oil.
FT-IR: 2980, 2925, 2888, 1639, 1556, 1510, 1452, 1357, 1273, 1192, 1002, 962, 927, 825, 763, 728, 700, 666.

Example 5

Iron(III)-tris(N,N-dibutyl-3-oxo-3-phenylpropanamidate)

3.53 g iron(III)-tris(acetylacetonate) and 8.34 g N,N-dibutyl-3-oxo-3-phenylpropanamide were reacted according to basic production procedure A. The result was 9.24 g of a red, highly viscous oil.
FT-IR: 2955, 2928, 2870, 1584, 1549, 1498, 1481, 1428, 1364, 1292, 1266, 1211, 1110, 1023, 917, 759, 732, 695.

Example 6

Iron(III)-tris(N,N-dibutyl-3-oxo-butanamidate)

3.53 g iron(III)-tris(acetylacetonate) and 6.61 g N,N-dibutyl-3-oxobutanamide were reacted according to basic production procedure A. The result was 7.50 g of a red, viscous oil.
FT-IR: 2955, 2928, 2870, 1598, 1557, 1511, 1461, 1429, 1366, 1291, 1267, 1228, 1199, 1155, 1111, 1007, 956, 762, 730, 697.

Example 7

Iron(III)-tris(N,N-dibutyl-3-oxo-heptanamidate)

3.53 g iron(III)-tris(acetylacetonate) and 7.92 g N,N-dibutyl-3-oxoheptanamide were reacted according to basic production procedure A. The result was 8.34 g of a red, viscous oil.
FT-IR: 2953, 2928, 2869, 1596, 1554, 1511, 1489, 1459, 1427, 1393, 1369, 1290, 1224, 1184, 1159, 1103, 1061, 959, 766, 730, 669.

Two-Component Polyurethane Compositions

Examples 8 to 9 and Comparison Examples V1 to V5

For each example, to produce the first component a polyethertriol (Voranol® CP 4755, from Dow) and a catalyst according to Table 1 were mixed intimately in a centrifugal mixer (SpeedMixer™ DAC 150, FlackTek Inc.) for a period of 30 sec. at 3000 rpm. Part of the freshly produced first component was then filled into an aluminum tube with a coated interior, which was then sealed air tight and stored for a period of 7 days in an air-circulating oven at 60° C.

The remaining portion of the freshly produced first component for each example was mixed in the described manner with a modified diphenylmethane diisocyanate that is fluid at room temperature (Desmodur® CD-L, from Bayer) as the second component according to Table 1 to produce a polyurethane composition.

For each example, the first component, which was stored at 60° C. for a period of 7 days, was likewise mixed in the same manner with the second component according to Table 1 to produce a polyurethane composition.

TABLE 1

Two-component polyurethane compositions (quantities in parts by weight).

| | Example | | | | | | |
|---|---|---|---|---|---|---|---|
| | 8 | 9 | V1 | V2 | V3 | V4 | V5 |
| First component: | | | | | | | |
| Voranol ® CP 4755 | 50 | 50 | 50 | 50 | 50 | 50 | 50 |
| Catalyst Example 2 | 0.13 | — | — | — | — | — | — |
| Catalyst Example 7 | — | 0.09 | — | — | — | — | — |
| Fe(acac)$_3$[a] | — | — | 0.21 | — | — | — | — |
| Iron octoate[b] | — | — | — | 0.75 | — | — | — |
| DBTDL[c] | — | — | — | — | 0.46 | — | — |
| Coscat ® 83[d] | — | — | — | — | — | 0.02 | — |
| DABCO 33-LV ®[e] | — | — | — | — | — | — | 0.10 |
| mmol-equiv./100 g[f] | 0.29 | 0.20 | 0.27 | 1.44 | 0.13 | 0.03 | 1.07 |
| Second component: | | | | | | | |
| Desmodur ® CD-L | 5.10 | 5.10 | 5.10 | 5.10 | 5.10 | 5.10 | 5.10 |

[a]25% suspension of iron(III)-tris(acetylacetonate) in N-ethylpyrrolidone.
[b]iron(III)-(2-ethylhexanoate) in 2-ethylhexanoic acid (6% Fe).
[c]10% solution of dibutyl tin dilaurate in diisodecyl phthalate.
[d]bismuth-tris(neodecanoate) in neodecanoic acid (16% Bi, from Erbsloh).
[e]33% solution of 1,4-diazabicyclo[2.2.2]octane in dipropylene glycol (from Air Products).
[f]mmol-equivalent metal atoms or amino groups of the catalyst in 100 g of the composition.

The polyurethane compositions were analyzed in terms of aspect, time to non-adhesion, bubble formation and Shore-A hardness, in each case both for the composition containing the freshly produced first component and for the composition containing the first component that was stored at 60° C. for a period of 7 days. Mechanical properties were measured in a tensile test only for the composition containing the freshly produced first component, before and after various storage periods to accelerate aging of the samples.

The aspect of the composition was assessed purely visually and was evaluated as "clear", "cloudy" or inhomogeneous" ("inh.").

To determine the time to non-adhesion (skin formation time), the compositions that were at room temperature were applied to pasteboard in a layer thickness of approximately 3 mm, and for each, the time until, when the surface of the composition was touched lightly with a pipette made of LDPE, no residue remains on the pipette was determined in a standard climate ("SC"; 23±1° C., 50±5% relative air humidity).

The formation of bubbles was assessed visually in terms of the number ("many", "some" or "none") of gas bubbles that developed in the composition that was used for determining the skin formation time during the curing of said composition.

Shore-A hardness was determined according to DIN 53505 in test samples that were cured over a period of 7 days in a standard climate.

To determine the mechanical properties in the tensile test, films of the composition measuring approximately 3 mm thick were produced by casting the composition in a flat PTFE mold, and curing these over a period of 7 days in a standard climate. Adhesion-free and flexible films were obtained. Dumb-bells measuring 75 mm in length, with a connector length of 30 mm and a connector width of 4 mm, were punched out of the films, and some of these were tested, according to DIN EN 53504, at a tensile speed of 200 mm/min for tensile strength, elongation at break and elasticity modulus (at 0.5 to 5.0% elongation). The remaining dumb-bells were stored for 1 day at 100° C. in an air-circulating oven, or for 10 days under "cataplasm" (40° C. and 100% relative air humidity), or for 10 days under "cataplasm" and 1 day at 100° C., after which each was held for one day in a standard climate and was tested as described, according to DIN EN 53504.

The results of these tests are presented in Table 2.

(Acclaim® 4200, from Bayer) and a catalyst according to Table 3 were intimately mixed in a centrifugal mixer (SpeedMixer™ DAC 150, FlackTek Inc.) for a period of 30 sec. at 3000 rpm. Part of the freshly produced first component was then filled into an aluminum tube with a coated interior, which was then sealed air tight and stored for a period of 7 days in an air-circulating oven at 60° C.

For each example, the remaining portion of the freshly produced first component was mixed in the manner described with a modified diphenylmethane diisocyanate that is fluid at room temperature (Desmodur® CD-L, from Bayer) as the second component according to Table 3 to produce a polyurethane composition.

For each example, the first component, which was stored at 60° C. for a period of 7 days, was likewise mixed in the same manner with the second component according to Table 3 to produce a polyurethane composition.

TABLE 2

Properties of the two-component polyurethane compositions

| | Example | | | | | | |
|---|---|---|---|---|---|---|---|
| | 8 | 9 | V1 | V2 | V3 | V4 | V5 |
| Composition with freshly produced first component: | | | | | | | |
| Aspect | clear | clear | inh. | clear | clear | clear | clear |
| Skin formation time (min.) | 32 | 20 | >180 | 40 | 10 | 3 | 15 |
| Shore-A hardness | 49 | 46 | 32 | 49 | 48 | 44 | 33 |
| Bubble formation | none | none | none | none | some | some | some |
| Tensile strength (MPa): | | | | | | | |
| 7 d/SC | 1.06 | 0.97 | 0.95 | 0.96 | 0.76 | 0.54 | 0.90 |
| +10 d/cataplasm | 0.89 | 0.92 | 0.94 | 0.85 | 0.71 | 0.79 | 0.82 |
| +1 d/100° C. | 0.91 | 0.86 | 0.84 | 0.76 | 0.60 | 0.73 | 0.86 |
| +10 d/cataplasm + 1 d/100° C. | 0.88 | 0.89 | 0.88 | 0.85 | 0.65 | 0.73 | 0.89 |
| Elongation at break (%): | | | | | | | |
| 7 d/SC | 82 | 69 | 80 | 107 | 65 | 42 | 100 |
| +10 d/cataplasm | 69 | 77 | 87 | 90 | 55 | 73 | 85 |
| +1 d/100° C. | 87 | 87 | 65 | 190 | 168 | 72 | 105 |
| +10 d/cataplasm + 1 d/100° C. | 80 | 84 | 84 | 118 | 170 | 74 | 108 |
| Elasticity modulus (MPa): | | | | | | | |
| 7 d/SC | 2.33 | 2.24 | 2.06 | 1.48 | 1.68 | 1.46 | 1.44 |
| +10 d/cataplasm | 1.82 | 1.66 | 1.75 | 1.48 | 1.68 | 1.56 | 1.47 |
| +1 d/100° C. | 1.77 | 1.73 | 1.96 | 0.47 | 0.60 | 1.49 | 1.23 |
| +10 d/cataplasm + 1 d/100° C. | 1.78 | 1.89 | 1.74 | 1.28 | 0.71 | 1.41 | 1.23 |
| Composition with stored first component: | | | | | | | |
| Aspect | clear | clear | inh. | clear | clear | clear | clear |
| Skin formation time (min.) | 35 | 25 | 100 | 240 | 10 | 45 | 15 |
| Shore-A hardness | 49 | 48 | 37 | 48 | 48 | 45 | 32 |
| Bubble formation | none | none | none | none | some | some | some |

As is clear from Table 2, the two-component polyurethane compositions containing the catalysts according to the invention are clear, homogeneous mixtures, which have relatively short skin formation times both before and after storage, and which cure free of bubbles to form a material of relatively high strength and good stability.

Examples 10 to 11 and Comparison Examples V6 to V10

For each example, to produce the first component a polyethertriol (Voranol® CP 4755, from Dow), a polyetherdiol

TABLE 3

Two-component polyurethane compositions (quantities given as percentages by weight).

| | Example | | | | | | |
|---|---|---|---|---|---|---|---|
| | 10 | 11 | V6 | V7 | V8 | V9 | V10 |
| First component: | | | | | | | |
| Voranol ® CP 4755 | 33.3 | 33.3 | 33.3 | 33.3 | 33.3 | 33.3 | 33.3 |
| Acclaim ® 4200 | 16.7 | 16.7 | 16.7 | 16.7 | 16.7 | 16.7 | 16.7 |
| Catalyst Example 2 | 0.15 | — | — | — | — | — | — |

TABLE 3-continued

Two-component polyurethane compositions
(quantities given as percentages by weight).

| | Example | | | | | | |
|---|---|---|---|---|---|---|---|
| | 10 | 11 | V6 | V7 | V8 | V9 | V10 |
| Catalyst Example 7 | — | 0.32 | — | — | — | — | — |
| Fe(acac)$_3$[a] | — | — | 0.21 | — | — | — | — |
| Iron octoate[b] | — | — | — | 0.90 | — | — | — |
| DBTDL[c] | — | — | — | — | 0.49 | — | — |
| Coscat ® 83[d] | — | — | — | — | — | 0.015 | — |
| DABCO 33-LV ®[e] | — | — | — | — | — | — | 0.14 |
| mmol-equiv./100 g[f] | 0.34 | 0.70 | 0.27 | 1.74 | 0.14 | 0.02 | 1.50 |
| Second component: | | | | | | | |
| Desmodur ® CD-L | 4.80 | 4.80 | 4.80 | 4.80 | 4.80 | 4.80 | 4.80 |

[a]25% suspension of iron(III)-tris(acetylacetonate) in N-ethylpyrrolidone.
[b]iron(III)-(2-ethylhexanoate) in 2-ethylhexanoic acid (6% Fe).
[c]10% solution of dibutyl tin dilaurate in diisodecyl phthalate.
[d]bismuth-tris(neodecanoate) in neodecanoic acid (16% Bi, from Erbsloh).
[e]33% solution of 1,4-diazabicyclo[2.2.2]octane in dipropylene glycol (from Air Products).
[f]mmol-equivalent metal atoms or amino groups of the catalyst in 100 g of the composition.

The polyurethane compositions were analyzed as described for Example 8 in terms of aspect, time to non-adhesion, bubble formation and mechanical properties in the tensile test, in each case only for the composition containing the freshly produced first component.

The results of these tests are presented in Table 4.

As is clear from Table 4, the two-component polyurethane compositions containing the catalysts according to the invention are clear, homogeneous mixtures which have relatively short skin formation times, and which cure free of bubbles to form a material of relatively high strength and good stability.

Examples 12 to 19

In the same manner as was described for Example 8, a polyethertriol (Voranol® CP 4755, from Dow) and a catalyst according to Table 5 were mixed in each case to produce the first component. Part of the freshly produced first component was then filled into an aluminum tube with a coated interior, which was then sealed air tight and stored for a period of 7 days in an air-circulating oven at 60° C.

The remaining portion of the freshly produced first component for each example was then mixed in the manner described for Example 8 with a modified diphenylmethane diisocyanate that is fluid at room temperature (Desmodur® CD-L, from Bayer) as the second component according to Table 5 to produce a polyurethane composition.

For each example, the first component that was stored at 60° C. for a period of 7 days was likewise mixed in the same manner with the second component according to Table 5 to produce a polyurethane composition.

The polyurethane compositions were analyzed as described for Example 8 in terms of aspect, time to non-adhesion, bubble formation, Shore-A hardness and mechanical properties in the tensile test.

TABLE 4

Properties of the two-component polyurethane compositions

| | Example | | | | | | |
|---|---|---|---|---|---|---|---|
| | 10 | 11 | V6 | V7 | V8 | V9 | V10 |
| Composition with freshly produced first component: | | | | | | | |
| Aspect | clear | clear | inh. | clear | clear | clear | clear |
| Skin formation time (min.) | 65 | 27 | 120 | 75 | 27 | 40 | 35 |
| Bubble formation | none | none | none | none | many | none | many |
| Tensile strength (MPa): | | | | | | | |
| 7 d/SC | 0.96 | 0.98 | 0.82 | 0.45 | 0.77 | 0.98 | 0.65 |
| +10 d/cataplasm | 0.95 | 0.96 | 0.77 | 0.38 | 0.77 | 0.89 | 0.66 |
| +1 d/100° C. | 0.90 | 0.84 | 0.89 | 0.55 | 0.48 | 0.83 | 0.72 |
| +10 d/cataplasm + 1 d/100° C. | 0.99 | 0.91 | 0.70 | 0.48 | 0.52 | 0.78 | 0.69 |
| Elongation at break (%): | | | | | | | |
| 7 d/SC | 130 | 124 | 129 | 94 | 105 | 117 | 135 |
| +10 d/cataplasm | 125 | 118 | 111 | 92 | 105 | 94 | 148 |
| +1 d/100° C. | 159 | 192 | 124 | 341 | 341 | 108 | 193 |
| +10 d/cataplasm + 1 d/100° C. | 161 | 125 | 103 | 152 | 303 | 96 | 181 |
| Elasticity modulus (MPa): | | | | | | | |
| 7 d/SC | 1.27 | 1.39 | 1.00 | 0.51 | 1.20 | 1.45 | 0.88 |
| +10 d/cataplasm | 1.41 | 1.67 | 1.06 | 0.60 | 1.30 | 1.56 | 0.81 |
| +1 d/100° C. | 1.09 | 0.75 | 1.33 | 0.14 | 0.20 | 1.34 | 0.69 |
| +10 d/cataplasm + 1 d/100° C. | 1.12 | 1.31 | 1.05 | 0.32 | 0.28 | 1.33 | 0.65 |
| Composition with stored first component: | | | | | | | |
| Aspect | clear | clear | inh. | clear | clear | clear | clear |
| Skin formation time (min.) | 73 | 32 | 105 | 300 | 30 | 210 | 35 |
| Bubble formation | none | none | none | some | some | some | some |

The results of these tests are presented in Table 6.

TABLE 5

Two-component polyurethane compositions.

| | Example | | | | | | | |
|---|---|---|---|---|---|---|---|---|
| | 12 | 13 | 14 | 15 | 16 | 17 | 18 | 19 |
| First component: | | | | | | | | |
| Voranol ® CP 4755 | 30 | 30 | 30 | 30 | 30 | 30 | 30 | 30 |
| Catalyst Example 2 | 0.28 | 0.08 | — | — | — | — | — | — |
| Catalyst Example 1 | — | — | 0.19 | — | — | — | — | — |
| Catalyst Example 3 | — | — | — | 0.50 | — | — | — | — |
| Catalyst Example 4 | — | — | — | — | 0.27 | — | — | — |
| Catalyst Example 5 | — | — | — | — | — | 0.34 | — | — |
| Catalyst Example 6 | — | — | — | — | — | — | 0.25 | — |
| Catalyst Example 7 | — | — | — | — | — | — | — | 0.30 |
| mmol-equiv./100 g$^a$ | 1.05 | 0.30 | 1.02 | 1.05 | 1.05 | 1.10 | 1.00 | 1.08 |
| Second component: | | | | | | | | |
| Desmodur ® CD-L | 3.10 | 3.10 | 3.10 | 3.10 | 3.10 | 3.10 | 3.10 | 3.10 |

$^a$mmol-equivalent iron atoms of the catalyst in 100 g of the composition.

TABLE 6

Properties of the two-component polyurethane compositions.

| | Example | | | | | | | |
|---|---|---|---|---|---|---|---|---|
| | 12 | 13 | 14 | 15 | 16 | 17 | 18 | 19 |
| Composition with freshly produced first component: | | | | | | | | |
| Aspect | clear | clear | clear | clear | clear | clear | clear | clear |
| Skin formation time (min.) | 13 | 18 | 6 | 20 | 16 | 30 | 6 | 6 |
| Shore-A hardness | 49 | 50 | 46 | 46 | 45 | 43 | 49 | 46 |
| Bubble formation | none | none | none | none | none | none | none | none |
| Composition with stored first component: | | | | | | | | |
| Aspect | clear | clear | clear | clear | clear | clear | clear | clear |
| Skin formation time (min.) | 15 | 20 | 7 | 22 | 15 | 27 | 6 | 5 |
| Shore-A hardness | 48 | 49 | 46 | 48 | 49 | 48 | 47 | 48 |
| Bubble formation | none | none | none | none | none | none | none | none |

As is clear from Table 6, the two-component polyurethane compositions containing the catalysts according to the invention are clear, homogeneous mixtures which have relatively short skin formation times both before and after storage, and which cure largely free of bubbles to form a material with good Shore-A hardness.

The invention claimed is:

1. Two-component polyurethane compositions, comprising at least one polyol as the first component, at least one polyisocyanate as the second component, and at least one iron(III) complex of the formula $Fe(L)_x(Y)_{3-x}$, in which
x stands for 1, 2 or 3,
Y stands for a uninegatively charged ligand, and
L stands for a ligand of formula (I),

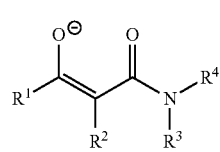

(I)

wherein
$R^1$ and $R^2$ independently stand for a hydrogen group or for a monovalent saturated or unsaturated hydrocarbon group having 1 to 10 carbon atoms, or together stand for a divalent alkylene group having 3 to 6 carbon atoms, and
$R^3$ and $R^4$ independently stand for a hydrogen group or for a monovalent saturated hydrocarbon group, optionally containing heteroatoms and having 1 to 12 carbon atoms, or together stand for a divalent alkylene group, optionally containing heteroatoms and having 3 to 6 carbon atoms.

2. The two-component polyurethane composition according to claim 1, wherein the polyol is a polyether polyol and the polyisocyanate is a diisocyanate.

3. The two-component polyurethane composition according to claim 1, wherein the iron(III) complex makes up 0.01 to 10 mmol-equivalent iron atoms to 100 g of the composition.

4. The two-component polyurethane composition according to claim 1, wherein the iron(III) complex is contained in the first component.

5. The two-component polyurethane composition according to claim 1 is a casting compound, sealant, adhesive agent, covering, coating, varnish, undercoating, molded element or elastomer.

6. A method in the production of a two-component polyurethane composition, comprising:
employing an iron(III) complex of the formula $Fe(L)_x(Y)_{3-x}$ as a catalyst in the production of a two-component polyurethane composition, where in the formula $Fe(L)_x(Y)_{3-x}$
x stands for 1, 2 or 3,
Y stands for a uninegatively charged ligand, and
L stands for a ligand of formula (I),

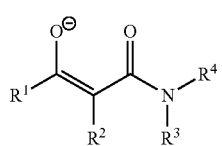

(I)

in which
$R^1$ and $R^2$ independently stand for a hydrogen group or for a monovalent saturated or unsaturated hydrocarbon group having 1 to 10 carbon atoms, or together stand for a divalent alkylene group having 3 to 6 carbon atoms, and
$R^3$ and $R^4$ independently stand for a hydrogen group or for a monovalent saturated hydrocarbon group, optionally containing heteroatoms and having 1 to 12 carbon atoms, or together stand for a divalent alkylene group, optionally containing heteroatoms and having 3 to 6 carbon atoms.

7. The method according to claim 6, wherein $R^1$ stands for an alkyl group having 1 to 4 carbon atoms or a phenyl group, or together with $R^2$ stands for a divalent alkylene group having 3 to 4 carbon atoms.

8. The method according to claim 6, wherein $R^2$ stands for a hydrogen group.

9. The method according to claim 6, wherein
$R^3$ stands for
    a hydrogen group,
    an alkyl group having 1 to 8 carbon atoms,
    a cycloalkyl group having 5 to 6 carbon atoms,
    a hydroxyalkyl group having 1 to 4 carbon atoms,
    an alkylether group having 1 to 4 carbon atoms, or
    together with $R^4$ stands for a divalent alkylene group of the formula $-(CH_2)_n-X-(CH_2)_n-$ with $X=O$, NR, in which
        R stands for a monovalent alkyl group having 1 to 4 carbon atoms, or S, and
        n=2 to 6.

10. The method according to claim 6, wherein $R^4$ stands for
a hydrogen group,
an alkyl group having 1 to 8 carbon atoms,
a cycloalkyl group having 5 to 6 carbon atoms,
a hydroxyalkyl group having 1 to 4 carbon atoms, or
an alkylether group having 1 to 4 carbon atoms.

11. The method according to claim 6, wherein x stands for 3.

* * * * *